US012635924B2

(12) United States Patent
Pang et al.

(10) Patent No.: US 12,635,924 B2
(45) Date of Patent: May 26, 2026

(54) WATER-REPELLENT ADHESIVE PATCH AND METHOD MANUFACTURING THE SAME

(71) Applicant: RESEARCH & BUSINESS FOUNDATION SUNGKYUNKWAN UNIVERSITY, Suwon-si (KR)

(72) Inventors: Changhyun Pang, Suwon-si (KR); Hyeongho Min, Suwon-si (KR); Jinhyung Kim, Suwon-si (KR); Da Wan Kim, Suwon-si (KR)

(73) Assignee: RESEARCH & BUSINESS FOUNDATION SUNGKYUNKWAN UNIVERSITY, Suwon-si (KR)

( * ) Notice: Subject to any disclaimer, the term of this patent is extended or adjusted under 35 U.S.C. 154(b) by 655 days.

(21) Appl. No.: 18/096,373

(22) Filed: Jan. 12, 2023

(65) Prior Publication Data

US 2023/0233126 A1    Jul. 27, 2023

(30) Foreign Application Priority Data

Jan. 26, 2022    (KR) ........................ 10-2022-0011194

(51) Int. Cl.
| | |
|---|---|
| *A61B 5/257* | (2021.01) |
| *A61B 5/01* | (2006.01) |
| *A61B 5/28* | (2021.01) |
| *B05D 1/12* | (2006.01) |
| *B05D 5/06* | (2006.01) |

(52) U.S. Cl.
CPC ................ *A61B 5/257* (2021.01); *A61B 5/01* (2013.01); *A61B 5/28* (2021.01); *B05D 1/12* (2013.01); *B05D 5/062* (2013.01); *A61B 2562/12* (2013.01); *B05D 2201/02* (2013.01)

(58) Field of Classification Search
CPC .. A61B 5/01; A61B 5/257; A61B 5/28; A61B 5/291; A61B 5/6832; A61B 5/6833; A61B 5/6834; A61B 2562/12; A61B 2562/164
See application file for complete search history.

(56) References Cited

U.S. PATENT DOCUMENTS

| | | | | |
|---|---|---|---|---|
| 2016/0206243 A1* | 7/2016 | Pang | .................... | A61B 5/6834 |
| 2020/0060541 A1* | 2/2020 | Andrade | ............ | A61B 5/14517 |
| 2020/0163844 A1* | 5/2020 | Pang | ...................... | A61K 8/733 |
| 2020/0261001 A1* | 8/2020 | Pang | ................. | A61B 5/14507 |
| 2022/0334076 A1* | 10/2022 | Shirai | ................ | G01N 27/3272 |

FOREIGN PATENT DOCUMENTS

| | | |
|---|---|---|
| KR | 10-2014-0043565 A | 4/2014 |
| KR | 10-2020-0075780 A | 6/2020 |
| KR | 10-2020-0099648 A | 8/2020 |

* cited by examiner

*Primary Examiner* — Bradford C. Blaise
(74) *Attorney, Agent, or Firm* — LEX IP MEISTER, PLLC

(57) ABSTRACT

Disclosed are a skin-attachable adhesive patch mimicking a leg structure of a diving beetle and having excellent skin-attachment ability even in a dry or wet condition, and a method for manufacturing the same. The skin-attachable adhesive patch includes a substrate; a plurality of negative pressure chambers formed on a surface of the substrate, wherein each of the plurality of negative pressure chambers has a truncated hollow sphere structure; a micro-wrinkle layer formed on at least a portion of a remaining area of the substrate except for an area thereof where the negative pressure chambers are formed; and a patterned carbon particle layer formed on the micro-wrinkle layer.

6 Claims, 6 Drawing Sheets

FIG. 1

WATER-REPELLENT ADHESIVE PATCH AND METHOD MANUFACTURING THE SAME

CROSS-REFERENCE TO RELATED APPLICATION

This application claims a benefit under 35 U.S.C. § 119(a) of Korean Patent Application No. 10-2022-0011194 filed on Jan. 26, 2022, on the Korean Intellectual Property Office, the entirety of disclosure of which is incorporated herein by reference for all purposes.

BACKGROUND

Field

The present disclosure relates to a water-repellent adhesive patch capable of exhibiting high adhesion, stretchability and durability in each of wet and/or dry environments, and a method for manufacturing the same.

The applicant of the present disclosure has developed a molding technology that inserts roots of conductive carbon particles (e.g., CNT) into a patch via a selective transfer process on an adhesive substrate having an intaglio structure having adsorption ability and a micro-wrinkle structure inspired from a diving beetle. Thus, the applicant of the present disclosure has developed a water-repellent skin-attachable adhesive patch that may be attached to and detached from a rough surface of a skin in different directions and may effectively discharge body wastes in wet and/or dry conditions to exhibit excellent adhesion.

Description of Related Art

Along with the rapid development of nanostructures and materials, stretchable wearable devices based on nanomaterials have recently attracted attention in the fields of diagnosis and treatment. These wearable devices may measure various biological signals such as electrocardiogram (ECG), electroencephalography (EEG), body temperature, pulse, blood sugar, and sweat pH in a long-term manner, and a real-time manner and may perform immediate monitoring thereon. In order to accurately measure human biological signals for a longer period of time, the wearable device requires (1) an electronic device element (e.g., an electrode or a sensor) with durability that may be applied to rough skin or dynamic environments, and (2) an adhesive interface technology that enables long-term effective body diagnosis even in various body environments and humid environments.

In order to maintain bio-signal measurement performance and function even under stretching or bending conditions, many studies have been conducted on conductive nanomaterials (metal nanowires, nanoparticles, and carbon-based particles). The carbon-based particles are used as a strong candidate because a simple solution treatment technique is applicable thereto, and carbon-based particles have the mechanical/chemical stability, and high conductivity. The carbon nanotube (CNT) material among the carbon-based particles has been widely used as a stretchable electronic material due to its high mechanical aspect ratio. A manufacturing method of a stretchable polymer composite using the widely known CNT includes a spray coating process and a simple mixing process. Although the spray coating process achieves high conductivity of the resulting composite, the resulting composite may have poor durability and may be easily damaged by continuous stretching or external contact. In addition, the simple mixing process is not able to form a polymer composite due to high CNT concentration. The resulting composite may not be practically used in the wearable device because it does not satisfy high stretchability and adaptability in dry/humid dynamic living organisms.

In addition, due to various skin environments such as stretching or bending during the movement of the human body, and moisture penetration into the body, the wearable device may not be uniformly attached to the skin in an entire sensed area. To solve this problem, previously reported wearable devices used chemical-based adhesives or moisture-dependent hydrogel materials. However, it is difficult to use repeatedly the chemical-based adhesive with low air permeability on sweaty or oily skin surfaces. When the chemical-based adhesive is attached to the skin for a long time, this may cause skin irritation or allergic reaction.

In consideration of the above descriptions, the durability/ electrical properties of stretchable electrodes for wearable devices, and dry/wet adhesives for continuous attachment for the wearable devices still have technical/material limitations. Therefore, there is a need for a wearable device that has stretchability, durability, conductivity and adhesiveness at the same time, and may maintain contact with the skin surface, and is manufactured using a simple manufacturing process. In order to achieve this need, a stable interface for the wearable device which occurs in an integrated two-dimensional plane with no gap between the electrode and the adhesive should be provided.

SUMMARY

This Summary is provided to introduce a selection of concepts in a simplified form that are further described below in the Detailed Description. This Summary is not intended to identify all key features or essential features of the claimed subject matter, nor is it intended to be used alone as an aid in determining the scope of the claimed subject matter.

The present disclosure proposes a method for developing a composite material of an electrode and a sensor with excellent durability and stretchability, and proposes a water-repellent skin-attachable adhesive patch which imitates a micro hierarchical structure that exists on a foreleg surface of a male diving beetle that may adhere well even in dry environments or underwater, and thus stably adheres to an inside/outside of a living body and stably measures body signals, and proposes a manufacturing method thereof.

A first purpose of the present disclosure is to provide an adhesive interface which imitates the hierarchical structure of the adsorption chamber and the micro-wrinkles on the surface of the diving beetle foreleg and thus is capable of strongly adhering to rough skin in a dry/aquatic environment while ensuring air-permeability. Introducing the micro-wrinkle on the adsorption chamber structure enables strong adhesion via drainage even in water via stronger hydrophobicity. Based on this technical idea, the present disclosure provides a creative design and manufacturing method of the adhesive patch optimized for dry/humid biological environments.

A second purpose of the present disclosure is to develop a manufacturing technology of a composite material that is stably conductive and stretchable by inserting the roots of the CNTs as the conductive material into the elastomeric polymer PDMS, and thus is to provide a novel material that overcomes the trade-off limit between durability and electrical properties of a conventional CNT/PDMS composite, and thus has excellent durability and electrical properties at the same time. This novel material may act as a basic element of the wearable device based on excellent stretchability and electrical performance to provide a stable device operation and bio-signal measurement.

A third purpose of the present disclosure is to develop an application technology in which a combination of the biomimetic adhesive structure and the stretchable conductive composite is applied. Specifically, the combination of the biomimetic adhesive structure and the stretchable conductive composite may be combined with various existing electronic and sensing materials to manufacture the skin-attachable wearable device which can detect and continuously monitor bio-signals such as body temperature, electrocardiogram (ECG), electroencephalogram (EEG), respiration, muscle tremors, and carotid artery activity information.

Purposes in accordance with the present disclosure are not limited to the above-mentioned purpose. Other purposes and advantages in accordance with the present disclosure as not mentioned above may be understood from following descriptions and more clearly understood from embodiments in accordance with the present disclosure. Further, it will be readily appreciated that the purposes and advantages in accordance with the present disclosure may be realized by features and combinations thereof as disclosed in the claims.

The water-repellent skin-attachable adhesive patch according to the present disclosure aims to provide excellent adhesion, electrical performance, and mechanical stability in each of dry and humid environments. The skin-attachable adhesive patch according to the present disclosure includes an adhesive structure that mimics the foreleg of the diving beetle, and a hydrophobic and stretchable electrode structure. Specifically, the skin-attachable adhesive patch according to the present disclosure includes a substrate; a plurality of negative pressure chambers formed on a surface of the substrate, wherein each of the plurality of negative pressure chambers has a truncated hollow sphere structure; a micro-wrinkle layer formed on at least a portion of a remaining area of the substrate except for an area thereof where the negative pressure chambers are formed; and a patterned carbon particle layer formed on the micro-wrinkle layer.

In accordance with the present disclosure, the wet environment means, for example, in-water, a wet surface, or a wet biological surface caused by perspiration.

In accordance with the present disclosure, the substrate refers to a flexible, elastic and/or air-permeable base plate used for the skin adhesive patch. The substrate may be embodied as a base (e.g., an elastic polymer) used in a conventional skin adhesive patch. Preferably, the substrate may be made of PDMS (Polydimethylsiloxane).

In accordance with the present disclosure, a truncated sphere structure means a shape in which a portion is cut from a full sphere such that a removed upper area cut along a cut face is smaller than a remaining lower area.

The negative pressure chamber according to the present disclosure induces the negative pressure to generate high adsorption ability, thereby providing strong adhesion in both dry and wet conditions. Further, a top face (the micro-wrinkle layer) acting as a bridge between the adjacent negative pressure chambers may prevent internal crack due to stress concentration to a center/middle area of the negative pressure chamber and inhibits crack propagation, resulting in strong adhesion.

In accordance with the present disclosure, a shape of the negative pressure chamber does not mean a shape of a full sphere, but means a truncated shape in which an upper portion (head) is cut away. In one embodiment, a diameter of the negative pressure chamber is smaller than a diameter of a full sphere.

In one embodiment, a hollow groove may be formed in the substrate and between the negative pressure chambers. The groove may be in a form of an isolated closed pore, and may be formed during manufacturing of the skin-attachable adhesive patch.

The micro-wrinkle layer in accordance with the present disclosure provides an improved surface area, which is an important parameter for improving capillary interactions on the wet surface and the van der Waals force on the dry surface. Further, the micro-wrinkle layer is closely adhered to the surface of the living body and discharges waste products such as sweat and excess water molecules under the capillary action of a groove between wrinkles. Thus, the micro-wrinkle layer according to the present disclosure provides high adhesion performance in each of the dry and/or wet conditions. Preferably, for easy discharge and adhesion, the micro-wrinkle layer according to the present disclosure may be formed on an entirety of a remaining area of the substrate surface except for an area of the substrate surface area where the negative pressure chambers are formed.

In one embodiment, the shape of the micro-wrinkle of the micro-wrinkle layer may be controlled so as to control the stretchability of the electrode. A larger wrinkle amplitude and wavelength may provide higher electrode stretchability. This may be because when stress is applied to the adhesive patch, a stress applied to the micro-wrinkle is consumed as energy to spread the wrinkled structure.

In one embodiment, the micro-wrinkle layer may have an isotropic micro-wrinkle structure in which the micro-wrinkles in an area from one end to the other end of the substrate are oriented in the same direction. The actual strain exerted by body movement is in multiple directions. Since anisotropic micro-wrinkles exhibit deformation characteristics in only one direction, the electrical resistance increases significantly as stretching in other directions is applied, such that the possibility of practical application is lowered. Therefore, preferably, the micro-wrinkle layer according to the present disclosure may have the isotropic micro-wrinkle structure in order to obtain stretchability that is insensitive to the patch deformation. Further, the isotropic micro-wrinkle structure may provide drainage ability similar to that of the anisotropic structure in a humid condition. This is because the adhesion increases in a humid environment such that the area of the isotropic micro-wrinkles may increase to increase a capillary force.

In one embodiment, the micro-wrinkle layer may be made of the same flexible, elastic and/or air-permeable material as the material constituting the negative pressure chamber and/or substrate. For example, the micro-wrinkle layer may be made of PDMS (Polydimethylsiloxane).

The carbon particle layer according to the present disclosure is a component that plays the role of an electrode in an adhesive patch. The carbon particle layer may be characterized by having stretchability, and may provide high electrical performance, water-repellent ability, and mechanical durability even under various external deformation conditions (external tensile deformation and hundreds to thousands of attachments and detachments).

In one embodiment, the carbon particle layer may be prepared by placing a patterned mask on a stretchable substrate in a stretched state, spraying a dispersion in which carbon particle powders are dispersed thereon, and then relaxing the stretchable substrate to restore the same to its original shape, and coating a polymer precursor on the stretchable substrate on which the patterned carbon particle layer has been formed and then stamping the stretchable substrate onto a surface of the micro-wrinkle layer. The carbon particle layer manufactured by the above method may be formed such that the roots of the plurality of carbon particles are embedded in the substrate and the remaining exposed portions thereof are irregularly entangled with each other to form a network. The network structure may maintain connectivity between the carbon particles even under externally applied force such as a stretching force, and thus may contribute to excellent electrical and mechanical properties of the water-repellent adhesive patch according to the present disclosure.

In one embodiment, the carbon particles may be one selected from carbon nanoparticles, carbon nanotubes (CNT), and carbon nanofibers (CNF). Preferably, the carbon particle may have a shape with a large aspect ratio. For example, the carbon particles in accordance with the present disclosure may be embodied as a multi-wall carbon nanoparticle (MWCNT).

The water-repellent skin-attachable adhesive patch according to the present disclosure may be used together with a sensor that measures temperature and/or an electro-cardiogram, etc., to continuously monitor biological changes. In addition, the sensor is characterized by monitoring activity information such as electroencephalogram (EEG), respiration, muscle tremors, and carotid artery.

A method for manufacturing the water-repellent skin-attachable adhesive patch according to the present disclosure includes: a first step of preparing a bridge structure, wherein the bridge includes a substrate; a plurality of negative pressure chambers formed on a surface of the substrate, wherein each of the plurality of negative pressure chambers has a truncated hollow sphere structure; and a micro-wrinkle layer formed on at least a portion of a remaining area of the substrate except for an area thereof where the negative pressure chambers are formed; a second step of placing a patterned mask on a stretchable substrate in a stretched state; spraying a dispersion in which carbon particle powders are dispersed; and relaxing the stretchable substrate to form the stretchable substrate having a patterned carbon particle layer formed thereon; a third step of coating a polymer precursor on the stretchable substrate on which the patterned carbon particle layer has been formed; attaching a surface of the micro-wrinkle layer of the bridge structure to the polymer precursor coating; and curing the polymer precursor coating; and a fourth step of detaching the stretchable substrate from the bridge structure.

In accordance with the present disclosure, the first step of preparing the bridge structure may include: preparing a master mold substrate having a plurality of intaglio pillar-shaped patterns defined therein, wherein a relief structure of a truncated sphere shape is formed in each of the plurality of intaglio pillar-shaped patterns; pouring and curing a first polymer precursor solution on the master mold substrate to obtain a polymer substrate having a plurality of relief pillars formed thereon, wherein each of the plurality of relief pillars has a groove of a truncated sphere shape defined therein; and immersing tips of the relief pillars of the polymer substrate in a second polymer precursor solution, withdrawing the polymer substrate out of the second polymer precursor solution, and stamping the polymer substrate onto a pattern substrate having micro-wrinkles formed thereon, thereby forming the micro-wrinkle layer on the polymer substrate. Preferably, the first and second polymer solutions may be made of the same material. A configuration of the bridge structure is substantially the same as that of the skin-attachable adhesive patch as described above, and thus redundant descriptions thereof will be omitted.

In accordance with the present disclosure, the second step is characterized by being performed using a solution-based selective transfer method. In accordance with the present disclosure, the selective transfer method refers to a method in which a dispersion of carbon particles is coated on a stretchable substrate in a stretched and tense state in multiple directions or in one direction, and then the stretchable substrate is relaxed and returned to its original state. The carbon particle layer coated using the selective transfer method may be formed such that the carbon particles are scattered in a particle form, but the carbon particles are entangled with each other to form a network structure. Specifically, the roots of the carbon particles are stably transplanted into the stretchable substrate, and the exposed portions of the carbon particles exposed out of the surface are connected to each other in all directions to form a three-dimensional matrix. The carbon particle layer coated on the stretchable substrate may maintain the matrix structure thereof even when the stretchable substrate is stamped onto the bridge structure. Therefore, when an external force is applied to the adhesive patch, connectivity between the carbon particles may be maintained, such that excellent electrical and mechanical properties of the adhesive patch according to the present disclosure may be easily achieved.

In accordance with the present disclosure, during the third step, the carbon particle layer is attached on the micro-wrinkle layer, and roots of the carbon particles are embedded in the micro-wrinkle layer, and remaining exposed portions of the carbon particles are irregularly entangled with each other to form a network.

In accordance with the present disclosure, during the fourth step, only the stretchable substrate is detached from the bridge structure while the coated patterned carbon particle layer is attached to the micro-wrinkle layer.

In one embodiment, the micro-wrinkle layer has an isotropic wrinkle structure in which micro-wrinkles in an entire area from one end to the other end of the substrate are oriented in the same direction.

In one embodiment, a mass content of the carbon particles of the skin-attachable adhesive patch may be in a range of about 0 exclusive to 40% exclusive relative to a total mass of the skin-attachable adhesive patch. When the mass content of the carbon particles is about 40% or larger, the electrical conductivity may be improved as the mass content increases, but there is no significant difference in the electrical conductivity. When the mass content of the carbon particles is excessive, a curing process may not be achieved reliably. The applicant of the present disclosure has identified that sufficient electrical conductivity for practical use is obtained even when the mass content of the carbon particles is smaller than about 40%. In order to simultaneously maintain the electrical and mechanical properties of the adhesive patch according to the present disclosure, the mass content of the carbon particles in accordance with the present disclosure may be in a range of about 10 to 20% based on the total mass of the patch.

According to the present disclosure, the water-repellent adhesive patch according to the present disclosure may exhibit stable adhesion, air permeability, and moisture control even in dynamic environmental conditions including a rough surface and moisture. Furthermore, the adhesive patch according to the present disclosure may be applied as a key source technology to promising industries such as wearable devices for diagnosis, and body-attached medical patches to improve diagnosis accuracy of various diseases. The sensor combined with the water-repellent adhesive patch according to the present disclosure may perform continuous monitoring. The water-repellent adhesive patch according to the present disclosure may be easily applied to a high-efficiency diagnosis system.

In addition to the effects as described above, specific effects in accordance with the present disclosure will be described together with following detailed descriptions for carrying out the disclosure.

BRIEF DESCRIPTION OF DRAWINGS

FIG. 1 is a diagram for illustrating a water-repellent adhesive patch according to the present disclosure and a method for manufacturing the patch. Specifically, in FIG. 1, (a) is an SEM image of a foreleg structure of a male diving beetle, (b) is a schematic diagram of an adhesive patch manufacturing method using a selective transfer method, (c) is a schematic diagram of an adhesive patch (APSE) having EGG and temperature sensors attached thereto, (d) is an image showing adhesion and high stretchability of the adhesive patch (APSE) onto wet (humid environment) human skin, and (e) is an SEM image showing an arrangement of an adhesive patch (APSE) structure.

In FIG. 3, each of (i) and (ii) is an enlarged SEM image of the structure (DIA-b) and (iii) is an enlarged SEM image of a micro-wrinkle layer of the structure (DIA-b).

DETAILED DESCRIPTIONS

Figure 2:
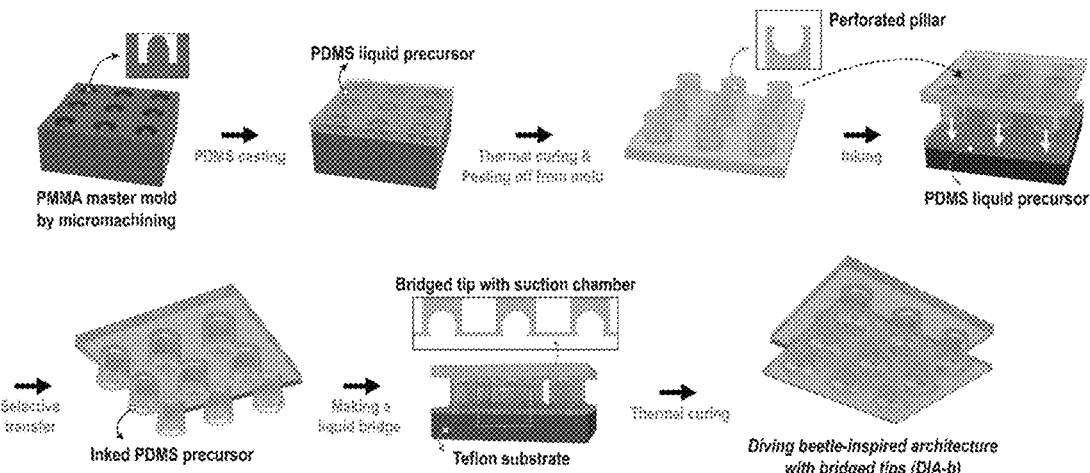
FIG. 2 is a diagram for illustrating a manufacturing method of a structure (DIA-b) inspired from a diving beetle according to an embodiment of the present disclosure.

For simplicity and clarity of illustration, elements in the drawings are not necessarily drawn to scale. The same reference numbers in different drawings represent the same or similar elements, and as such perform similar functionality. Further, descriptions and details of well-known steps and elements are omitted for simplicity of the description. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure. Examples of various embodiments are illustrated and described further below. It will be understood that the description herein is not intended to limit the claims to the specific embodiments described. On the contrary, it is intended to cover alternatives, modifications, and equivalents as may include within the spirit and scope of the present disclosure as defined by the appended claims.

A shape, a size, a ratio, an angle, a number, etc. disclosed in the drawings for illustrating embodiments of the present disclosure are illustrative, and the present disclosure is not limited thereto. The same reference numerals refer to the same elements herein. Further, descriptions and details of well-known steps and elements are omitted for simplicity of the description. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

The terminology used herein is for the purpose of describing particular embodiments only and is not intended to limit the present disclosure. As used herein, the singular forms "a" and "an" are intended to include the plural forms as well, unless the context clearly indicates otherwise. It will be further understood that the terms "comprise", "comprising", "include", and "including" when used in this specification, specify the presence of the stated features, integers, operations, elements, and/or components, but do not preclude the presence or addition of one or more other features, integers, operations, elements, components, and/or portions thereof. As used herein, the term "and/or" includes any and all combinations of one or more of the associated listed items. Expression such as "at least one of" when preceding a list of elements may modify the entirety of list of elements and may not modify the individual elements of the list. When referring to "C to D", this means C inclusive to D inclusive unless otherwise specified.

It will be understood that, although the terms "first", "second", "third", and so on may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

In addition, it will also be understood that when a first element or layer is referred to as being present "on" or "beneath" a second element or layer, the first element may be disposed directly on or beneath the second element or may be disposed indirectly on or beneath the second element with a third element or layer being disposed between and connected to the first and second elements or layers. It will be understood that when an element or layer is referred to as being "connected to", or "coupled to" another element or layer, it may be directly on, connected to, or coupled to the other element or layer, or one or more intervening elements or layers may be present. In addition, it will also be understood that when an element or layer is referred to as being "between" two elements or layers, it may be the only element or layer between the two elements or layers, or one or more intervening elements or layers may also be present.

Further, as used herein, when a layer, film, region, plate, or the like may be disposed "on" or "on a top" of another layer, film, region, plate, or the like, the former may directly contact the latter or still another layer, film, region, plate, or the like may be disposed between and connected to the former and the latter. As used herein, when a layer, film, region, plate, or the like is directly disposed "on" or "on a top" of another layer, film, region, plate, or the like, the former directly contacts the latter and still another layer, film, region, plate, or the like is not disposed between and connected to the former and the latter. Further, as used herein, when a layer, film, region, plate, or the like may be disposed "below" or "under" another layer, film, region, plate, or the like, the former may directly contact the latter or still another layer, film, region, plate, or the like may be disposed between and connected to the former and the latter. As used herein, when a layer, film, region, plate, or the like is directly disposed "below" or "under" another layer, film, region, plate, or the like, the former directly contacts the latter and still another layer, film, region, plate, or the like is not disposed between and connected to the former and the latter.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In one example, when a certain embodiment may be implemented differently, a function or operation specified in a specific block may occur in a sequence different from that specified in a flowchart. For example, two consecutive blocks may be actually executed at the same time. Depending on a related function or operation, the blocks may be executed in a reverse sequence.

In descriptions of temporal relationships, for example, temporal precedent relationships between two events such as "after", "subsequent to", "before", etc., another event may occur therebetween unless "directly after", "directly subsequent" or "directly before" is not indicated.

The features of the various embodiments of the present disclosure may be partially or entirely combined with each other, and may be technically associated with each other or operate with each other. The embodiments may be implemented independently of each other and may be implemented together in an association relationship.

Spatially relative terms, such as "beneath," "below," "lower," "under," "above," "upper," and the like, may be used herein for ease of explanation for illustrating one element or feature's relationship to another element or feature as illustrated in the figures. It will be understood that the spatially relative terms are intended to encompass different orientations of the device in use or in operation, in addition to the orientation depicted in the figures. For example, when the device in the drawings may be turned over, elements described as "below" or "beneath" or "under" other elements or features would then be oriented "above" the other elements or features. Thus, the example terms "below" and "under" may encompass both an orientation of above and below. The device may be otherwise oriented, for example, rotated 90 degrees or at other orientations, and the spatially relative descriptors used herein should be interpreted accordingly.

Figure 1:
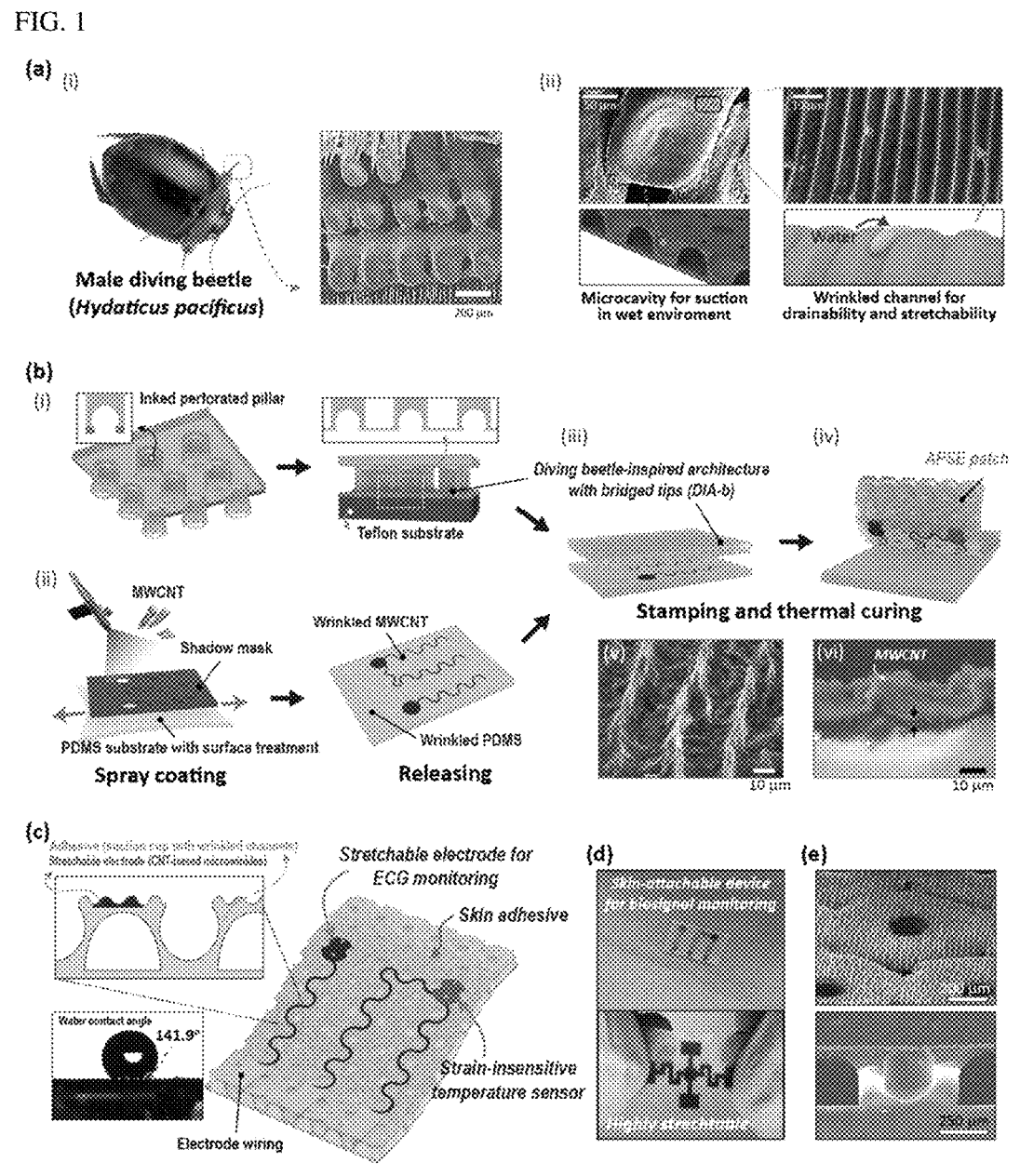

FIG. 1 is a diagram for illustrating an adhesive patch according to the present disclosure and a method for manufacturing the same.

Referring to (a) of FIG. 1, the adhesive patch according to the present disclosure was manufactured by imitating the adsorption and micro-wrinkle structure of the male diving beetle (Cybister japonicus) foreleg. The male diving beetle's shallow suckers and grooved spatula bristles use a bonding mechanism of capillary interaction for adsorption, viscous resistance, and adhesion, allowing the male to attach to the female's back during mating in an aquatic environment. That is, a intaglio cup-shaped chamber structure of the diving beetle induces a negative pressure in the water to realize stable adhesion ((a) (i) of FIG. 1). Further, the diving beetle's micro-wrinkle structure adheres closely to the substrate and releases excess water molecules through the micro-wrinkle grooves under a capillary action. Thus, the micro-wrinkle structure together with the cup-shaped chamber structure achieve effective adhesion ((a) (ii) of FIG. 1). The present disclosure is inspired from this natural adhesive system. Thus, the applicant of the present disclosure has developed the adhesive patch including a regular array structure of mushroom-shaped pillars with micro-cavities and micro-wrinkle structures, using manufacturing techniques such as mold forming and selective transfer methods.

Referring to (b) of FIG. 1, the adhesive patch according to the present disclosure is manufactured based on a following process. First, in order to prepare a carbon particle layer as an electrode, a patterned MWCNT is prepared. The patterned MWCNT is manufactured by placing a patterned mask on a stretched PDMS substrate and spray-coating a solution in which the MWCNTs are dispersed on the stretched PDMS substrate. The MWCNT may be selected as an electrode material in accordance with the present disclosure because it has high mechanical and chemical stability, and a simple solution process for composite material application is applicable thereto. After the MWCNT coating has been performed, the stretching applied to the PDMS substrate is removed, such that the surface of the PDMS substrate is wrinkled, and at the same time the coated MWCNT layer is also wrinkled ((b) (ii) of FIG. 1). In order to manufacture the remaining structure of the adhesive patch according to the present disclosure except for the above resulting structure, a substrate including a relief pillar having a groove formed therein is manufactured using a master mold. Then, the substrate is immersed in a polymer precursor solution, such that the polymer precursor is inked on a tip portion of the relief pillar of the substrate. Then, the tip portion of the relief pillar on which the polymer precursor is inked is lightly pressed using a Teflon substrate on which a micro-wrinkle is formed. During this process, the tip portions of the relief pillars may be connected to each other under a capillary bridging effect to form a polymer layer structure. The surface of the polymer layer may have the micro-wrinkle formed thereon by the Teflon substrate. In addition, micro-cavity is formed in a polymer layer area corresponding to the groove inside the relief pillar, such that a negative pressure chamber inducing a negative pressure for adsorption may be formed. Then, using a curing process, a structure (DIA-b) inspired from a diving beetle is manufactured ((b) (i) of FIG. 1) (A detailed manufacturing process thereof will be described in detail with reference to FIG. 2 below). The adhesive patch according to the present disclosure may be manufactured by stamping the patterned MWCNT and the structure (DIA-b) inspired from the diving beetle. Specifically, a PDMS precursor is poured onto the PDMS substrate having the patterned MWCNT layer, and a face of the diving beetle-inspired structure (DIA-b) where the negative pressure chamber is formed is stamped. Then, when a curing step is performed and the PDMS substrate having the MWCNT layer is detached therefrom, the adhesive patch (APSE) according to the present disclosure is formed. As may be seen in the image of (b) of FIG. 2, it may be identified that the adhesive patch (APSE) manufactured via the manufacturing method of the present disclosure has a pattern array of high integrity and fidelity of the micro-wrinkle layer and the wrinkled and patterned MWCNT layer.

Referring to (c) in FIG. 1 which shows a schematic diagram of the adhesion chamber of the present disclosure, the adhesive patch according to the present disclosure includes a wrinkled structure composed of MWCNT and PDMS. This surface shape of the adhesive patch may improve the surface area and provide smooth electrode connection of the outermost layer. The adhesive patch may be composed of a periodic structure with an optimized dimension (diameter 500 μm, height 300 μm, spacing 300 μm) in a uniform arrangement. Due to the selectively transferred MWCNT, the adhesive patch exhibits a water contact angle (CA<141.9°) and high water-repellent property.

Referring to (d) of FIG. 1 where the adhesive patch according to the present disclosure is applied to the human skin, the adhesive patch according to the present disclosure may be uniformly attached to wet human skin, and allows excess water molecules to be discharged from the wet human skin. The adhesive patch according to the present disclosure includes the PDMS as the polymer matrix which has high flexibility (Young's modulus (E) being about 500 kPa). Therefore, the PDMS-based composite material may be attached to the skin due to stretchability, flexibility, and biocompatibility properties.

Referring to (e) of FIG. 1, the SEM image of the adhesive patch array according to the present disclosure and a side view of a single DIA-bw with high integrity and uniformity are shown. It may be identified that the adhesive patch has a micro-wrinkle controlled in one direction and micro cavities for the negative pressure.

FIG. 2 is a diagram for illustrating a manufacturing method of a structure (DIA-b) inspired from a diving beetle according to an embodiment of the present disclosure.

Referring to FIG. 2, a method for forming the structure (DIA-b) inspired from the diving beetle according to the present disclosure includes pouring a PDMS polymer precursor solution onto a master mold substrate having a plurality of intaglio pillar-shaped patterns, wherein a spherical relief structure is formed inside each of the plurality of intaglio pillar-shaped patterns, and curing the PDMS polymer precursor solution to manufacture a PDMS substrate in which a plurality of relief pillars, each having a groove defined therein, are formed. The tip portions of the relief pillars of the PDMS substrate are immersed in the viscous PDMS polymer precursor solution, such that the polymer precursor solution is inked onto the tip of each of the relief pillars (Inked PDMS precursor). Then, the tip portion of the relief pillar where the polymer precursor is present is slightly pressed using a Teflon substrate having a micro-wrinkle structure formed thereon. Thus, a polymer layer in which the tip portions of the relief pillars are connected to each other via the polymer precursor may be formed. The polymer layer may have a micro-wrinkle structure on the surface thereof. The micro-cavity may be formed in the polymer layer area corresponding to the groove inside the relief pillar to form a negative pressure chamber for inducing the negative pressure for adsorption.

Figure 3:
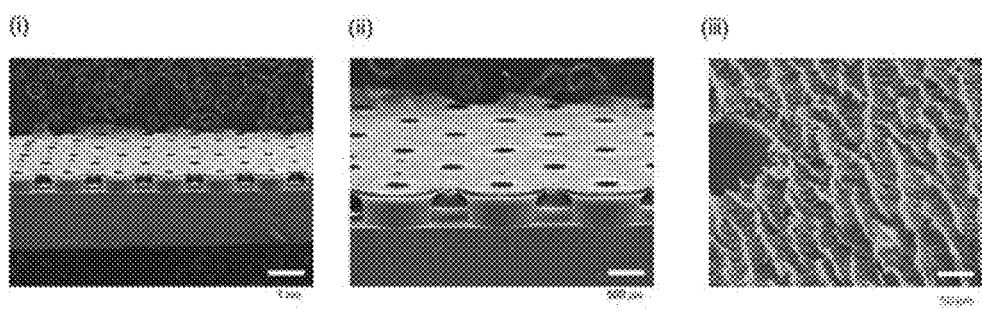
FIG. 3 is a SEM image showing a structure of a structure (DIA-b) inspired from a diving beetle as manufactured according to an embodiment of the present disclosure.

FIG. 3 is a SEM image showing a structure of a structure (DIA-b) inspired from a diving beetle as manufactured according to an embodiment of the present disclosure. In FIG. 3, each of (i) and (ii) is an enlarged SEM image of the structure (DIA-b), and (iii) is an enlarged SEM image of a micro-wrinkle layer of the structure (DIA-b).

Referring to FIG. 3, it may be identified that the negative pressure chamber and the wrinkle structure are well formed on the surface of the structure (DIA-b) inspired from the diving beetle according to the present disclosure.

Hereinafter, an adhesive patch according to the present disclosure and a method for manufacturing the same will be described in detail based on Present Example and Comparative Example. However, Present examples of the present disclosure are merely some embodiments of the present disclosure, and the scope of the present disclosure is not limited to the following Present Examples.

EXPERIMENTAL EXAMPLE

1. Evaluation of Characteristics Based on MWCNT Electrode Deposition Method

Figure 5:
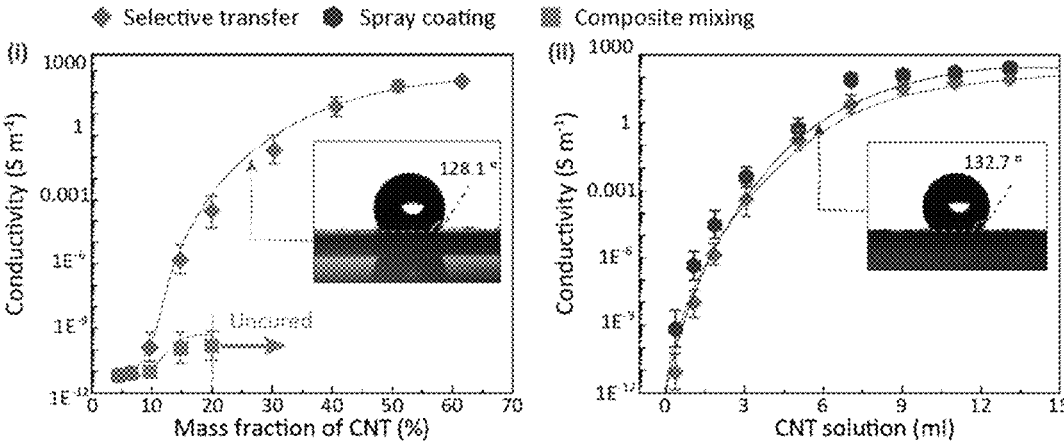
FIG. 5 is a diagram showing electrical conductivity based on the carbon particle (MWCNT) deposition method of the present disclosure. (i) is a diagram of a comparing result between the electrical conductivities based on the mass fraction of CNT of samples respectively manufactured via the selective transfer method and the complex mixing method, (ii) is a diagram of a comparing result between the electrical conductivities based on a mass of the CNT solution of samples respectively manufactured via the selective transfer method and the spray coating method. In each diagram, an inset shows a contact angle (CA) of water.
Figure 6:
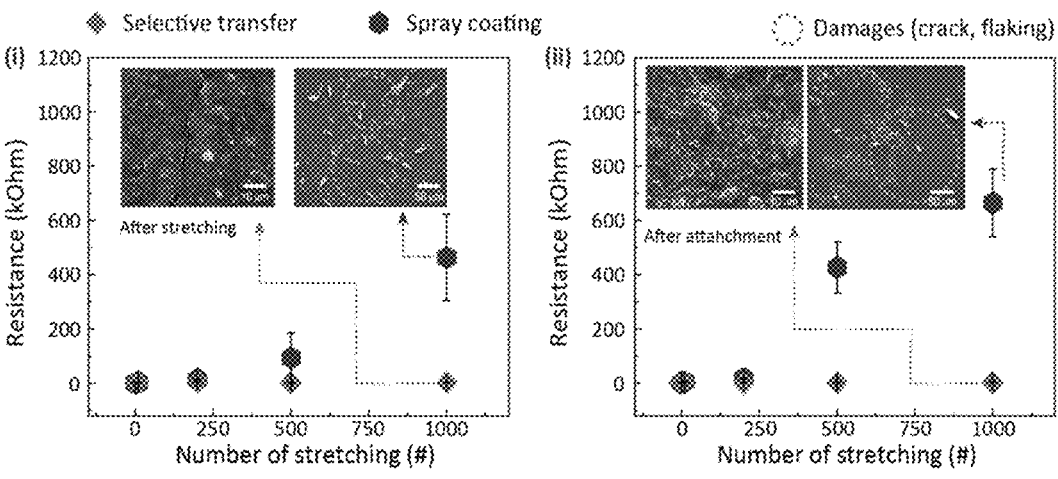
FIG. 6 is a diagram for evaluating the mechanical durability of a sample manufactured based on the carbon particle (MWCNT) deposition method of the present disclosure. (i) shows electrical resistance after applying 1000 times of repeated stretching to a sample manufactured via each of the selective transfer method and the spray coating method. (ii) shows electrical resistance after performing 1000 times of attachment and detachment of a sample manufactured via each of the selective transfer method and the spray coating method.

The electrical and mechanical properties of the samples based on the methods (selective transfer method, spray coating, and complex mixing process) of depositing the MWCNT on PDMS were evaluated. The evaluation results are shown in FIG. 4 to FIG. 6, respectively.

Surface Analysis

Figure 4:
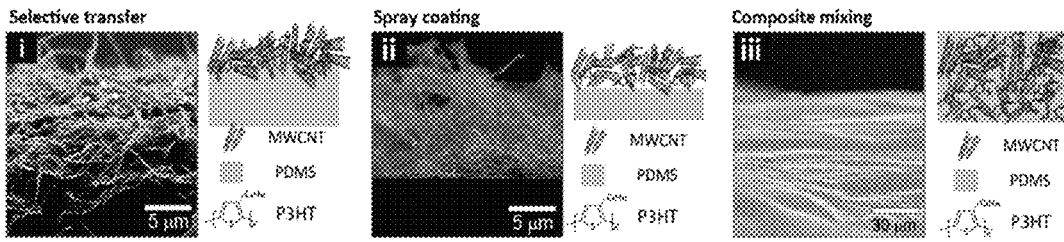
FIG. 4 is a SEM image of a cross-sectional structure based on a carbon particle (MWCNT) deposition method of the present disclosure. (i) represents a cross-sectional structure of a sample manufactured via selective transfer, (ii) represents a cross-sectional structure of a sample manufactured via spray coating, and (iii) represents a cross-sectional structure of a sample manufactured via composite mixing.

Referring to FIG. 4, it may be identified that in a sample manufactured by the selective transfer method of the present disclosure, the roots of MWCNTs are embedded in the PDMS, and the remaining portions of the MWCNTs in a bulky state are present on the PDMS surface. The portions of MWCNTs exposed out of the surface contact each other in all directions to form a nanoscale buckled three-dimensional matrix. The roots of the MWCNTs are stably implanted into PDMS while the MWCNTs are not scattered in a form of particles or not lost.

On the contrary, it may be identified that in the sample manufactured via the spray coating process, MWCNTs were deposited so as to be separated from PDMS, rather than deposited so as to be mechanically and/or chemically bonded to the surface of PDMS. It may be identified that in the sample manufactured via the complex mixing process, the MWCNT particles are embedded in the PDMS layer.

Analysis of Electrical Conductivity and Contact Angle

Referring to FIG. 5, it may be identified that in the selective transfer and spray coating processes, the electrical conductivity increases as the concentration of MWCNTs increases, and that due to the hydrophobic nature of MWCNTs, the water contact angle (CA) is large, resulting in excellent water-repellent properties.

Measurement of Durability Against Stretching and Adhesion

To analyze the mechanical durability, 1000 times of repeated stretching (to 30%) and 1000 times of attachment and detachment are performed. The results are shown in FIG. 6.

Referring to FIG. 6, it may be identified that in the selective transfer method, an initial level of electrical resistance and mechanical durability against external stimuli such as repetitive stretching and attachment is achieved. On the contrary, it may be identified that in the spray coating, the electrical resistance increases significantly, and defects are observed in the sample.

Through the above experiments, it may be identified that the adhesive patch manufactured via the selective transfer method of the present disclosure exhibits sufficient durability against external stimuli such as stretching and adhesion.

2. Evaluation of Characteristic Based on Type of Micro-Wrinkle

Figure 7:
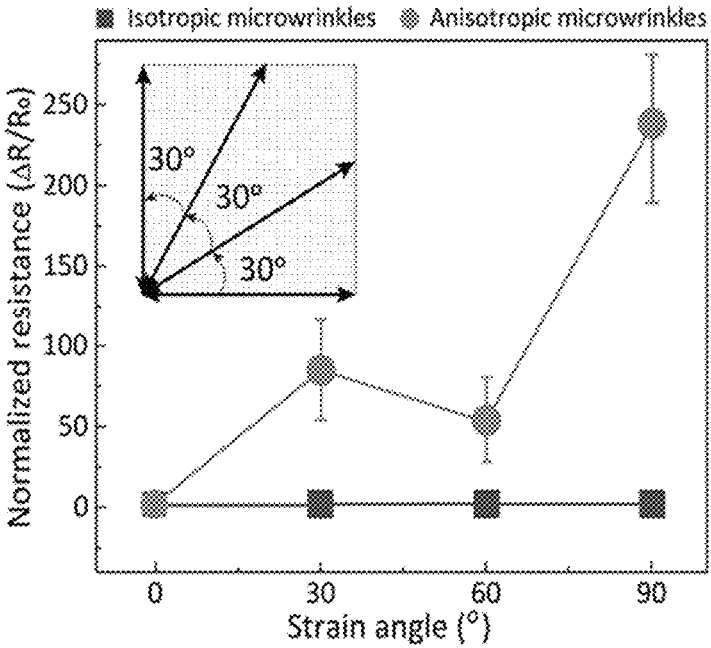
FIG. 7 is a diagram evaluating electrical characteristics under tensile strain in various directions based on a micro-wrinkle type (anisotropic micro-wrinkles and isotropic micro-wrinkles) of the present disclosure.
Figure 8:
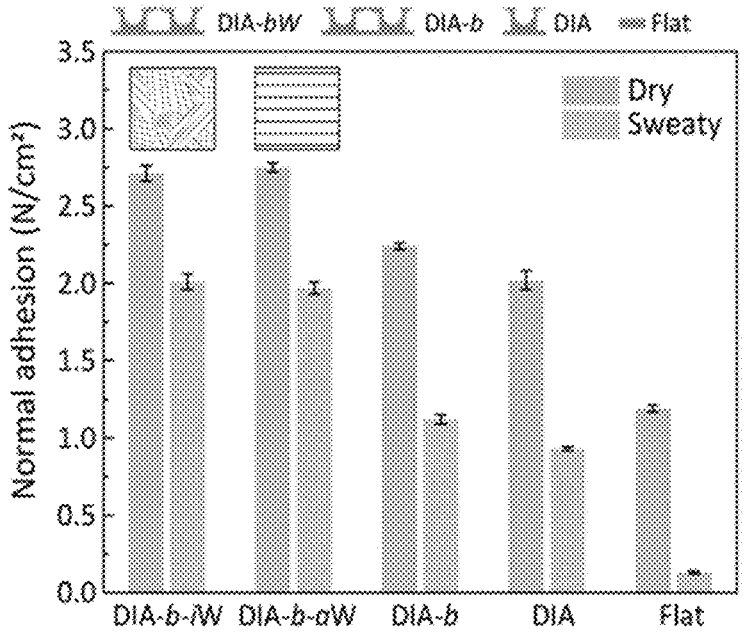
FIG. 8 is a graph showing adhesive performance under 100 repeated cycles of detachment and attachment in dry and sweaty wet conditions based on the micro-wrinkle type of the present disclosure.

Electrical and mechanical properties are evaluated based on the type of the micro-wrinkle according to the present disclosure, and the results are shown in FIG. 7 and FIG. 8.

Electrical Conductivity Analysis

Referring to FIG. 7, it may be identified that in the anisotropic micro-wrinkles, stable conductivity is maintained only at horizontally stretching (0°), and the electrical resistance increases significantly at stretching in other directions (30°, 60°, 90°). In particular, at stretching at 90°, the anti-deformation ability is lost, and a large change in electrical resistance occurs. On the contrary, it may be identified that in the isotropic micro-wrinkles, electrical conductivity is stably maintained at stretching in all directions of 0°, 30°, 60° and 90°.

Adhesion Performance Measurement

The cyclic pull-off adhesive ability of DIA-bw is measured for repeated cycles of detachment and attachment in each of wet and dry conditions.

Referring to FIG. 8, it is identified that the adhesive performances of the anisotropic micro-wrinkles and the isotropic structures are similar to each other in each of the dry and humid environments. However, the wrinkle-free structure exhibits poor adhesive ability in each of the dry and humid environments.

3. Evaluation of Adhesion of APSE Device

In order to evaluate the characteristics of the adhesive patch (APSE) according to the present disclosure, adhesion ability is analyzed while repeating cycles of detachment and attachment from and to each of the pig skin and the Si wafer under each of the wet and/or dry conditions. A simple cleaning is performed using a scotch tape at each specific cycle, and adhesion measurement values are measured per a cycle of 100 detachment-attachments after cleaning.

Figure 9:
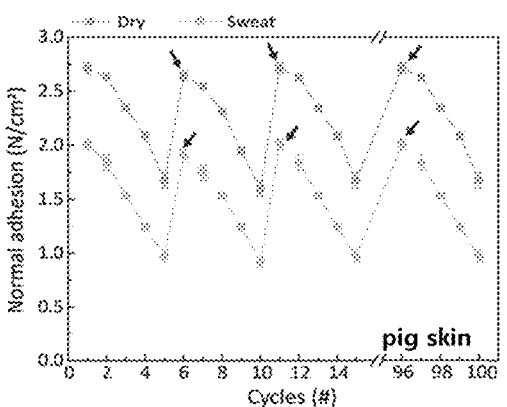
FIG. 9 shows adhesive performance to a pig skin and a Si wafer of an adhesive patch (APSE) of the present disclosure to which a sensor is attached, under wet and/or dry conditions.
Figure 9:
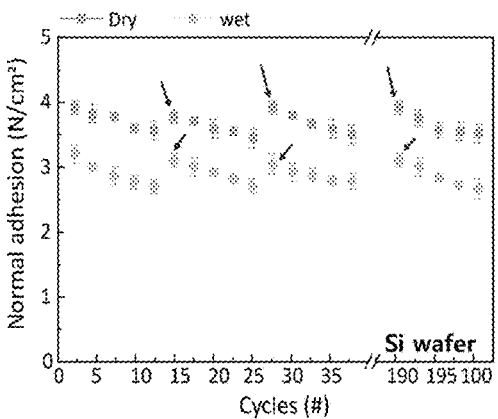

Referring to FIG. 9, it is shown that the adhesive patch exhibits high repeatability of detachment and attachment under each of the wet and dry conditions. In other words, it may be identified that the adhesive patch according to the present disclosure has high stretchability and adhesion on each of the wet and dry skins.

4. Application of APSE for Medical Monitoring

Figure 10:
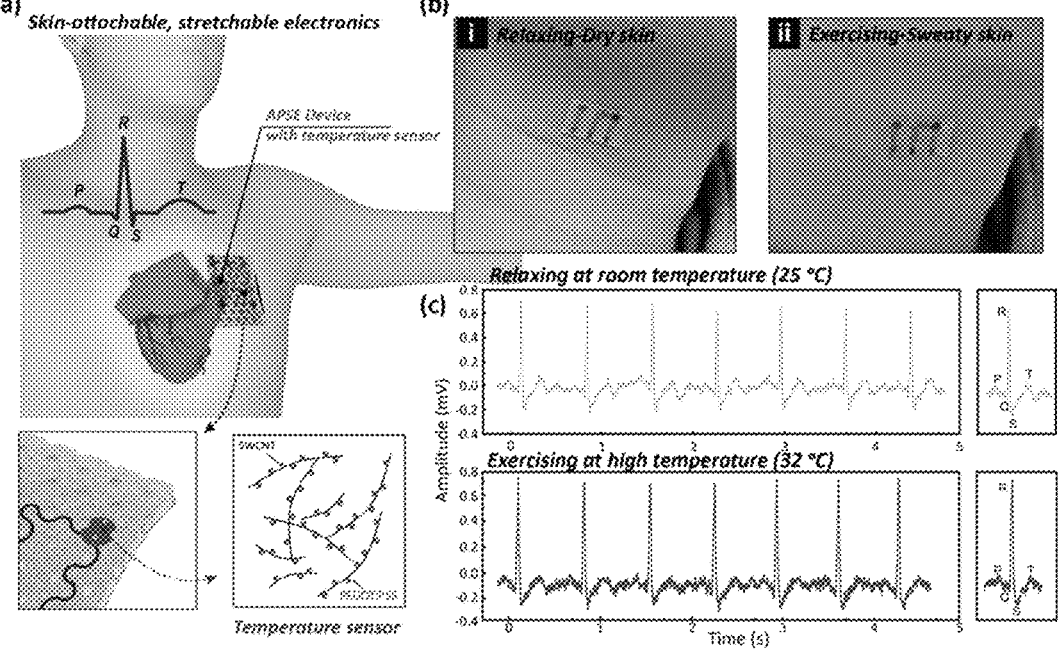
FIG. 10 is a diagram showing application of the adhesive patch (APSE) of the present disclosure for medical monitoring. (a) is a schematic diagram of an adhesive patch (APSE) with a temperature sensor attached thereto, (b) show images of the APSE attached before and after exercise, respectively, and (c) show EGG signals measured by APSE during exercise and relaxation, respectively.

FIG. 10 shows the actual application of the APSE to a bio-signal monitoring device on dry or sweaty skin in daily life. In FIG. 10, (a) is a schematic diagram of an adhesive patch (APSE) with a temperature sensor attached thereto, (b) show images of the APSE attached before and after exercise, respectively, and (c) show EGG signals measured by APSE during exercise and relaxation, respectively.

FIG. 10 shows the ECG signal and human body temperature measured using a temperature sensor (PEDOT: PSS, CNT, and PU composite) that is insensitive to deformation and is attached to the human body. The temperature sensor composite is coated between the MWCNT/PDMS composite electrodes of APSE. To verify the performance of APSE in various environments, large external loads/strains/pressures are applied to the device while humidity in the environment is increased by perspiration and body temperature is raised due to exercise. The APSE is conformally/uniformly attached to the human body in each of the dry and humid environments, and the ECG signal and body temperature are measured as shown in (b) in FIG. 10. As shown in (c) in FIG. 10, the ECG signal is monitored during exercise.

Referring to FIG. 10, in an environment where continuous human motion occurs and the body sweats, the APSE is maintained to be firmly attached to the body, and is insensitive to the strain of the device, and reliable and accurate ECG monitoring is achieved due to isotropic stretchability and drainage properties. In the relaxation, the experiment is conducted at room temperature (about 25° C.), and light exercise (70 bpm, walking) is conducted at a rather high temperature (about 32° C.) to analyze the performance on the sweaty skin surface and the movement of the skin. ECG signals measured in bent and wet conditions provide meaningful results on biomedical information related to cardiovascular disease based on factors such as P waves, PR intervals, QRS complexes, ST segments, T waves, and corrected QT intervals derived from the P, Q, R, S, and T waves that define heart rate and frequency.

Figure 11:
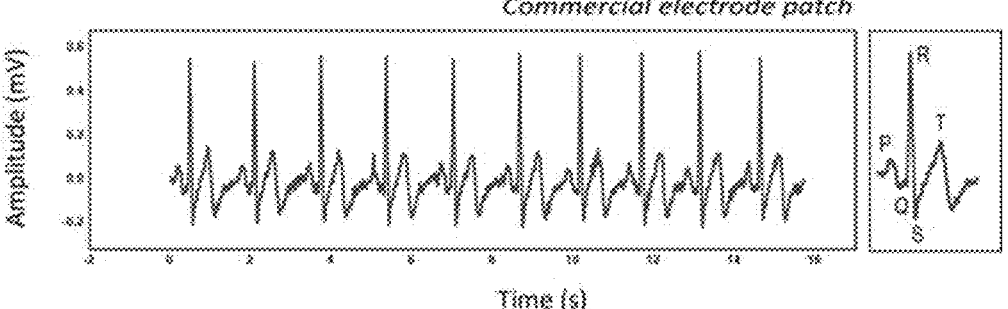
FIG. 11 shows EGG signals during exercise and relaxation respectively as obtained from a commercially available EGG sensing electrode.

Referring to FIG. 11 together with the results of (c) in FIG. 10, it may be identified that the ECG signal ((c) in FIG. 10) obtained with the APSE flexible electrode is similar to the signal (FIG. 11) obtained from the commercial ECG detection electrode.

Figure 12:
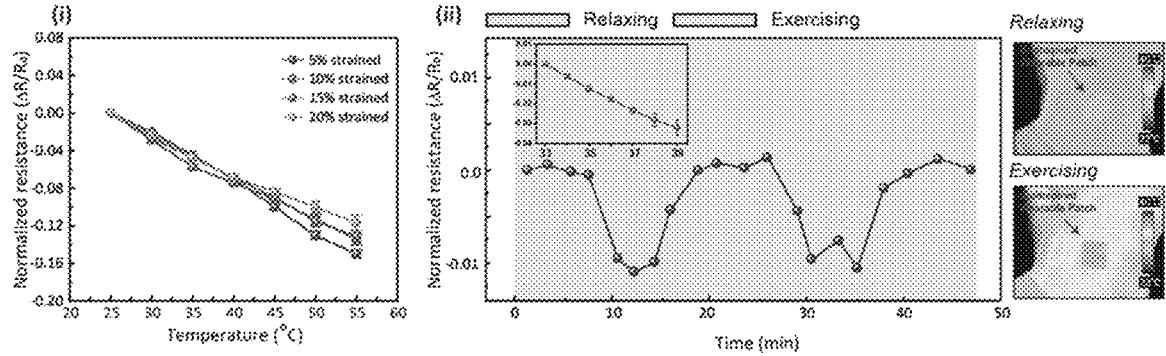
FIG. 12 is a diagram showing a result of measuring a temperature of the human body using an adhesive patch (APSE) of the present disclosure to which a temperature sensor is attached. (i) is an electrical resistance of each of temperature sensors (single-wall CNT, PEDOT:PSS, and PU) based on a temperature under an applied tensile strain. (ii) is an electrical signal detection result of the APSE based on change in a body temperature during repetitive exercise and relaxation, and a result of body temperature measurement with an existing commercial temperature sensor.

FIG. 12 is a diagram showing a result of measuring a temperature of the human body using an adhesive patch (APSE) of the present disclosure to which a temperature sensor is attached. (i) is an electrical resistance of each of temperature sensors (single-wall CNT, PEDOT:PSS, and PU) based on a temperature under an applied tensile strain. (ii) is an electrical signal detection result of the APSE based on change in a body temperature during repetitive exercise and relaxation, and a result of body temperature measurement with an existing commercial temperature sensor.

Referring to (i) of FIG. 12, a linear response in which the APSE is not sensitive to deformation due to the isotropic micro-wrinkle structure is achieved. The electrical resistance of the thin film composite (PEDOT:PSS-MWCNT) reacts sensitively to external temperature. All of the thin film composites (PEDOT:PSS-MWCNT) are sensitive to external temperature due to the corresponding temperature coefficient of resistance and electron hopping at the interface between PEDOT:PSS and CNT.

Referring to (ii) in FIG. 12, while the user is running or relaxes, body temperature change is continuously measured by APSE with a built-in temperature sensor. The result is compared with that obtained using commercially available temperature sensor equipment (testo 870, Testo, Inc) as shown in a right image (relaxing, exercising image). The temperature corresponding to the initial resistance value as measured by the APSE with a built-in temperature sensor according to the present disclosure is 35.5° C., and temperature rise up to 36° C. is reversibly measured by the APSE with a built-in temperature sensor according to the present disclosure during the exercise.

According to the present disclosure, the adhesive patch may be manufactured via multifunctional carbon particle (CNT) implantation and an easy solution process to obtain an isotropic micro-wrinkle structure. The form of the adhesive patch may be controlled such that the adhesive patch with the carbon nanotubes implanted therein exhibits durable conductivity for bioelectronics that may be attached to the skin. The combination thereof with the adsorption structure that mimics the diving beetle exhibits high adhesive strength in both dry and wet environments of the skin. Finally, under the experiments, bio-signal monitoring such as the bio-signal such as the body temperature and ECG is successfully performed using the sensor (APSE) including the adhesive patch according to the present disclosure. The adhesive patch in accordance with the present disclosure as inspired from the foreleg structure of a male diving beetle may contribute to the development of skin-attached and wearable biomedical skin patches for various healthcare applications in the future.

Although the present disclosure has been described above with reference to the preferred embodiment of the present disclosure, those skilled in the art will be able to understand that the present disclosure may be variously modified and changed without departing from the spirit and area of the present disclosure as described in the claims below.

What is claimed is:

1. A skin-attachable adhesive patch comprising:
a substrate;
a plurality of negative pressure chambers formed on a surface of the substrate, wherein each of the plurality of negative pressure chambers has a truncated hollow sphere structure;
a micro-wrinkle layer formed on at least a portion of a remaining area of the substrate except for an area thereof where the plurality of negative pressure chambers are formed; and
a patterned carbon particle layer formed on the micro-wrinkle layer,
wherein the patterned carbon particle layer is formed such that roots of a plurality of carbon particles are embedded in the micro-wrinkle layer and remaining exposed portions thereof are irregularly entangled with each other to form a network.

2. The skin-attachable adhesive patch of claim 1, wherein the patterned carbon particle layer is formed by:
placing a patterned mask on a stretchable substrate in a stretched state;
spraying a dispersion in which carbon particle powders are dispersed onto the stretchable substrate;
relaxing the stretchable substrate to restore the stretchable substrate to an original shape;
coating a polymer precursor on the stretchable substrate on which the patterned carbon particle layer has been formed; and
stamping the stretchable substrate having the coated polymer precursor formed thereon onto a surface of the micro-wrinkle layer.

3. The skin-attachable adhesive patch of claim 1, wherein each of the plurality of carbon particles is a multi-wall carbon nanoparticle.

4. The skin-attachable adhesive patch of claim 1, wherein the micro-wrinkle layer has a wrinkle structure in which micro-wrinkles throughout the micro-wrinkle layer are oriented in the same direction.

5. The skin-attachable adhesive patch of claim 1, wherein a diameter of the truncated hollow sphere structure of each of the plurality of negative pressure chambers is smaller than a diameter of a full sphere from which the truncated hollow sphere structure is formed.

6. The skin-attachable adhesive patch of claim 1, wherein a hollow groove is formed in the substrate and between adjacent negative pressure chambers of the plurality of negative pressure chambers.

* * * * *